United States Patent [19]
Gruetzmacher et al.

[11] Patent Number: 5,458,910
[45] Date of Patent: Oct. 17, 1995

[54] LOW CALORIE FAT SUBSTITUTE

[75] Inventors: Gordon D. Gruetzmacher, Groton; Jeffrey W. Raggon, Uncasville; Bishop Wlodecki, Preston, all of Conn.

[73] Assignee: Pfizer Inc., New York, N.Y.

[21] Appl. No.: 253,187

[22] Filed: Jun. 2, 1994

Related U.S. Application Data

[63] Continuation of Ser. No. 975,222, Nov. 12, 1992, abandoned, which is a continuation of Ser. No. 720,989, Jun. 25, 1991, abandoned.

[51] Int. Cl.⁶ .................................................. A23D 9/007
[52] U.S. Cl. ........................................ 426/611; 426/804
[58] Field of Search .................................. 426/601, 611, 426/804

[56] References Cited

U.S. PATENT DOCUMENTS

| | | | |
|---|---|---|---|
| 3,600,186 | 8/1971 | Mattson | 426/804 |
| 3,649,647 | 3/1972 | Ota et al. | 260/345.8 |
| 3,963,699 | 6/1976 | Rizzi et al. | 260/234 R |
| 5,021,256 | 6/1991 | Guffey | 426/601 |
| 5,158,796 | 10/1992 | Bernhardt | 426/804 |

FOREIGN PATENT DOCUMENTS

| | | |
|---|---|---|
| 375027 | 6/1990 | European Pat. Off. . |
| 281631 | 11/1987 | Japan . |
| 63-267715 | 11/1988 | Japan . |
| 1223667 | 3/1971 | United Kingdom . |
| 1457569 | 12/1976 | United Kingdom . |
| 9101322 | 7/1991 | WIPO . |

*Primary Examiner*—Carolyn Paden
*Attorney, Agent, or Firm*—Peter C. Richardson; Gregg C. Benson; Robert F. Sheyka

[57] ABSTRACT

There is disclosed a low calorie fat substitute comprising a sorbitol fatty acid ester with a degree of substitution of about four fatty acid groups. Foodstuffs containing the sorbitol tetraester are also disclosed.

49 Claims, No Drawings

LOW CALORIE FAT SUBSTITUTE

This application is a continuation of U.S. Ser. No. 07/975,222, filed Nov. 12, 1992, now abandoned, which is a continuation of U.S. Ser. No. 07/720,989, filed Jun. 25, 1991, now abandoned.

BACKGROUND OF THE INVENTION

The present invention relates to low calorie fat substitutes.

Continued concern with the health problems, e.g. obesity, arteriosclerosis, etc., associated with a diet high in fat content has led to new formulations of normally high-caloric fat-containing foods. These formulations are often referred to as "diet," "lite" and "low calorie" and are made by replacement of the normally present fat with non-fat ingredients such as air, water, or protein, etc., thereby reducing the fat content. Due to the reduction in fat content, there is often a corresponding reduction in the perceived quality of the food.

Another approach which has been suggested is to modify the fat to alter its absorption characteristics. This approach entails reducing the susceptibility of the fat to digestion by intestinal lipase enzymes; the theory being that if the fat is not absorbed, the material will be non-caloric. This approach of fat modification is referred to in a number of patents and patent applications.

U.S. Pat. No. 3,600,186 to Mattson refers to low calorie fat-containing food compositions wherein from about 10 percent to about 100 percent of the fat consists of a sugar fatty acid ester having at least 4 fatty acid ester groups or a sugar alcohol fatty acid ester which is completely esterified. One compound exemplified in the Mattson patent is a mixed sucrose octaoleate. Since this compound was a liquid polyester, an undesirable anal-leakage effect was noted.

U.S. Pat. No. 4,005,195 refers to the combination of a liquid polyol polyester with an anti-anal leakage (AAL) agent. The AAL agents mentioned are edible $C_{12}$ and higher saturated fatty acids, sources of edible $C_{12}$ and higher saturated fatty acids and solid polyol fatty acid polyesters.

U.S. Pat. No. 4,005,196 refers to the combination of a liquid polyol fatty acid polyester, an AAL and fat soluble vitamins to overcome the undesirable vitamin depletion observed when liquid polyol polyesters are used as fat substitutes in foods.

U.S. Pat. No. 4,927,658 refers to trishydroxymethyl alkane ester derivatives, notably fatty acid and dicarboxylate-extended fatty acid esters of monomeric and dimeric trishydroxymethyl alkanes, as low calorie fat substitutes, or fat mimetics, as these modified fats in general are now called.

U.S. Pat. No. 4,927,659 refers to the use of the fatty acid esters of trishydroxymethyl ethane and trishydroxymethyl propane as fat mimetics.

U.S. Pat. No. 4,959,466 refers to partially esterified polysaccharides (PEP) such as xanthan gum, guar gum, pectin, etc. transesterified with fatty acid methyl esters.

U.S. Pat. No. 2,962,419 refers to esters of neopentyl type alcohols such as pentaerythritoltetracaprylate as fat substitutes.

U.S. Pat. No. 3,579,548 refers to fat substitutes which are made by replacing the fatty acids attached to glycerol with alternate acids.

U.S. Pat. No. 3,495,011 refers to the administration of polyglycerols and polyglycerol esters as a means for lowering blood cholesterol.

U.S. Pat. No. 3,158,490 refers to a salad oil having 0.001% of a dissolved disaccharide ester.

U.S. Pat. No. 1,656,474 refers to an edible composition consisting essentially of ethyl margarate, glyceryl margarate and fat-soluble vitamins.

U.S. Pat. No. 3,353,966 refers to a salad oil containing an oligosaccharide or disaccharide esterified with a hydroxy fatty acid and a saturated fatty acid.

Patent Cooperation Treaty (PCT) Application No. W090/00012 refers to a fatty composition comprising a blend of a polyol fatty acid polyester and a glyceride fat having a specified steepness.

U.S. Pat. No. 4,810,516 refers to a reduced calorie chocolate confection comprising cocoa, an artificial sweetener, a carbohydrate bulking agent and a polyol fatty acid polyester.

U.S. Pat. No. 4,034,083 refers to a composition comprising a polyol fatty acid polyester and a fat soluble vitamin.

European Patent (EP) Application No. 342,972 refers to comminuted meat products containing polyol fatty acid polyesters.

EP Application No. 290,420 refers to shortening compositions containing polyol fatty acid polyesters having a certain melting point, liquid polyol fatty acid polyesters, and hardstock fat.

EP Application No. 290,216 refers to the use of polyol fatty acid polyesters for the treatment of ulcers.

PCT Application No. 90/00014 refers to a frying fat composition containing a glyceride fat and a polyol fatty acid polyester.

U.S. Pat. No. 4,849,242 refers to polyoxyalkylene fatty acid esters as low calorie fat substitutes.

EP Application No. 348,196 refers to granola bars, popcorn clusters and other food pieces which are held together by a binder which is preferably a sucrose polyester.

EP Application No. 236,288 refers to intermediate melting sucrose polyesters useful as low calorie fat substitutes.

PCT Application No. WO 90/00013 refers to blends of nondigestible polyol fatty acid polyesters having a slip melting point of greater than 25° C. and a transition time of greater than 60 seconds.

U.S. Pat. No. 4,508,746 refers to a low calorie edible oil which is a tricarballylic acid esterified with saturated or unsaturated alcohols having straight or branched chains of from 8 to 30 carbon atoms.

U.S. Pat. Nos. 4,582,927 and 4,673,581 refer to certain diesters, e.g. hexadecyl dioleylmalonate and dihexadecyl dioleylmalonate, useful as low calorie fat substitutes.

U.S. Pat. No. 4,582,715 refers to certain alpha-acylated glycerides useful as low calorie fat substitutes.

U.S. Pat. No. 4,461,782 refers to baked products containing a non-absorbable non-digestible liquid polyol polyester, microcrystalline cellulose and a solid polyol polyester of a solid fatty acid as an AAL agent.

EP Application No. 405874 refers to fatty acid diesters of various dihydric alcohols containing 4 to 10 carbon atoms and the use of the diesters as fat substitutes.

European Patent Application No. 352907 refers to a fat substitute composition comprising a liquid polyol fatty acid polyester, at least 10% of a solid low calorie fat substitute and at least 1% of a cohesive network of polysaccharide fibrils and microfibrils by weight of the liquid polyester.

EP Application No. 233856 refers to a low calorie fat substitute comprising (a) an edible, wholly or partially digestible fat material having specified properties, and (b) an edible food material, preferably an emulsifier, which acts as a solvent for the fat material.

U.S. Pat. No. 4,497,864 refers to a magnetic recording medium having ferromagnetic particles in a binder which contains at least one anhydrosorbitol di- and/or tetra-fatty acid non-hydroxy ester.

EP Application No. 375239 refers to an emulsified salad oil dressing containing a mixture of a low calorie fat material and a triglyceride oil.

EP Application No. 350981 refers to a hard fat substitute useful for confectionery manufacture, comprising a polyol fatty acid polyester having fatty acid residues derived from fully hardened vegetable oils.

EP Application No. 350983 refers to fat substitutes comprising a blend of a polyol fatty acid polyester and a glyceride fat, with the blend especially useful in layered dough products.

EP Application No. 350986 refers to a fat composition comprising a blend of a polyol fatty acid polyester and a glyceride fat, the fat composition exhibiting improved air entrapment upon whipping.

EP Application No. 350987 refers to a fatty composition comprising a blend of polyol fatty acid polyesters having a slip melting point of above 25° C.

EP Application No. 350988 refers to a frying fat composition comprising a blend of a non-digestible polyol fatty acid polyester and a glyceride fat with the blend having a specified slip melting point.

EP Application No. 354600 refers to an edible fat-containing product comprising two distinct fat phases: a fat phase containing an edible polyol fatty acid polyester, and a fat phase consisting essentially of a digestible fat and an oil soluble vitamin, with a vitamin-impervious phase separating the two fat phases.

EP Application No. 375031 refers to the use of non-fermentable dietary fibers as AAL agents.

EP Application No. 377237 refers to low-calorie confectionery products wherein a substantial proportion of the fat material consists of indigestible polyol fatty acid polyesters.

EP Application No. 378876 refers to low-calorie confectionery products containing indigestible polyol fatty acid polyesters, wherein at least 30% of the polyesters are unsaturated fatty acids trans hardened to a level of over 30%.

EP Application No. 379747 refers to spreads containing a fat phase of indigestible polyol fatty acid polyester, glyceride fats, and a gelled aqueous phase.

SUMMARY OF THE INVENTION

In one embodiment, the present invention is directed to a sorbitol fatty acid ester with a degree of substitution of about 4 fatty acid groups derived from a mixture of fatty acids provided that not all of said fatty acid groups are derived from oleic acid, said composition useful as a low calorie fat substitute.

Preferred is the composition wherein the degree of substitution ranges from about 3.6 to about 4.4 fatty acid groups, with an especially preferred degree of substitution of about 3.8.

Especially preferred is the composition wherein at least a portion of said ester is in the anhydride form.

Preferred is the composition wherein said fatty acid groups are selected from the group consisting of synthetic, natural, saturated, unsaturated, straight or branched chain fatty acids, and mixtures thereof.

Preferred is the composition wherein said fatty acid groups of said fatty acid ester are selected from the group consisting of butyric, caproic, caprylic, pelargonic, capric, undecanoic, lauric, myristic, myristoleic, palmitoleic, ricinoleic, erucic, palmitic, stearic, arachidic, behenic, oleic, elaidic, linoleic, linolenic, eleostearic and arachidonic acids; fatty acid derivatives; and mixtures thereof.

Especially preferred is the composition wherein said fatty acid groups are obtained from oils selected from the group consisting of non-hydrogenated, partially hydrogenated, and hydrogenated oils selected from the group consisting of soybean oil, safflower oil, sunflower oil, sesame oil, peanut oil, corn oil, olive oil, rice bran oil, rapeseed oil, canola oil, shea nut oil, babassu nut oil, coconut oil, palm kernel oil, cottonseed oil, and palm oil; butterfat, tallow and lard; and mixtures thereof.

Especially preferred is the composition wherein said fatty acid groups are obtained from hydrogenated, partially hydrogenated, or non-hydrogenated soybean oil.

In another embodiment, the present invention is directed to a triglyceride-containing foodstuff having at least a portion of the normally present triglyceride replaced by a sorbitol fatty acid ester with a degree of substitution of about 4 fatty acid groups.

Preferred foodstuffs are those wherein at least a portion of said sorbitol fatty acid ester is in the anhydride form. Preferred foodstuffs within which the sorbitol fatty acid ester replaces at least a portion of the normally present triglyceride are frozen desserts, salad dressings, or salad oils, dips for crackers, chips or vegetables, spreads, whipped toppings, triglyceride-containing confections, frostings or icings for cakes or cookies, fillings for cakes or cookies, whipped or gelled desserts, puddings, beverages, shortenings, frying oils, soups, baked goods, mayonnaise or imitation mayonnaise, liquid or dry imitation dairy products, liquid or plastic margarine spreads, gravies, sauces, pasta, sprays for cooking or frying, coatings for snack foods, and, meat, poultry, or fish analogues.

In another embodiment, the present invention is directed to a method of reducing the fat content of a foodstuff containing triglycerides comprising replacing at least a portion of the normally present triglyceride by a composition comprising a sorbitol fatty acid ester with a degree of substitution of about 4 fatty acid groups. Preferred is the method wherein at least a portion of said sorbitol fatty acid ester is in the anhydride form.

Preferred foodstuffs which have their fat content reduced by the method of the present invention are frozen desserts, salad dressings, salad oils, dips for crackers, chips or vegetables, spreads, whipped toppings, triglyceride containing confections, frostings or icings for cakes or cookies, fillings for cakes or cookies, whipped desserts, gelled desserts, puddings, beverages, shortenings, frying oils, soups, baked goods, mayonnaise or imitation mayonnaise, liquid or dry imitation dairy products, liquid or plastic margarine spreads, gravies, sauces, pasta, sprays for cooking or frying, coatings for snack foods, and, meat, poultry, or fish analogues.

In another embodiment, the present invention is directed to a process for preparing a mixture of sorbitol fatty acid esters and sorbitol anhydride fatty acid esters with a degree of substitution of about 4 fatty acid groups comprising: heating a mixture of sorbitol, an alkali metal fatty acid soap, an excess, based on the weight of sorbitol, of a fatty acid alkyl ester, and a basic catalyst, to a temperature and for a time sufficient to effect the desired degree of esterification.

In another embodiment, the present invention is directed to the sorbitol esters and sorbitol anhydride esters produced by the above process.

Preferred catalysts are alkali metal catalysts, with preferred alkali metal catalysts selected from the group consisting of alkali metals, alkali metal hydrides, alkali metal hydroxides, alkali metal alkoxides and alkali metal carbonates; and combinations thereof.

Especially preferred catalysts are selected from the group consisting of potassium metal, sodium metal, potassium hydride, sodium hydride, potassium hydroxide, sodium hydroxide, potassium methoxide, potassium ethoxide, potassium t-butoxide, sodium methoxide, sodium ethoxide, potassium carbonate and sodium carbonate; and combinations thereof.

Especially preferred catalysts are sodium carbonate and potassium carbonate.

Especially preferred fatty acid alkyl esters are fatty acid methyl esters.

In another embodiment, the present invention is directed to the sorbitol esters and sorbitol anhydride esters produced by the above process.

DETAILED DESCRIPTION OF THE INVENTION

The sorbitol fatty acid ester of the present invention has a degree of substitution of about 4, preferably from about 3.6 to about 4.4, most preferably about 3.8. By degree of substitution of about 4 is meant that of the hydroxyl groups available for esterification, about four are esterified.

Sorbitol is a six carbon sugar alcohol which contains six hydroxyl groups available for esterification. In the present invention, sorbitol is esterified on about 4 of the hydroxyl groups with a fatty acid containing from about 4 to about 22 carbon atoms. Examples of such fatty acids include butyric, caprylic, caproic, capric, lauric, myristic, pelargonic, myristoleic, palmitic, palmitoleic, stearic, oleic, ricinoleic, undecanoic, linoleic, linolenic, eleostearic, elaidic, arachidic, arachidonic, behenic and erucic acid. The fatty acids may be naturally occurring or synthetic fatty acids; they may be saturated or unsaturated, including positional and geometrical isomers; they may be straight chain or branched chain fatty acids. Mixtures of fatty acids may also be used, such as those obtained from non-hydrogenated, partially hydrogenated, or hydrogenated soybean, safflower, sunflower, sesame, peanut, corn, olive, rice bran, canola, babassu nut, coconut, palm kernel, shea nut, cottonseed, rapeseed, or palm oil; or butterfat, tallow or lard.

The fatty acid may also be a fatty acid derivative such as, for example an alpha-acylated fatty acid as described in U.S. Pat. No. 4,582,715, an alpha-branched fatty acid as described in U.S. Pat. No. 3,579,548, or an extended fatty acid formed by reacting a fatty alcohol with a dicarboxylic acid. Examples of suitable dicarboxylic acids which may be reacted with the fatty alcohol to form said extended fatty acid are malonic, succinic, glutaric and adipic acids. The resulting extended fatty acids are, structurally, $ROCOCH_2COOH$ from malonic acid, $ROCO(CH_2)_2COOH$ from succinic acid, $ROCO(CH_2)_3COOH$ from glutaric acid, $ROCO(CH_2)_4COOH$ from adipic acid, and the like, where R is the fatty alcohol radical.

The sorbitol fatty acid tetraester can be prepared by a variety of methods well known by those skilled in the art. These methods include transesterification of sorbitol with methyl, ethyl or glycerol fatty acid esters using a variety of methods well known to those skilled in the art, acylation of sorbitol with a fatty acid chloride, acylation of sorbitol with a fatty acid anhydride and acylation of sorbitol with a fatty acid, mixtures of fatty acids, or a fatty acid derivative.

Depending on the method by which the sorbitol fatty acid ester is made, it contains varying proportions of esterified sorbitol anhydrides. For example, when esterification is carried out by acylation with a fatty acid chloride, the product contains very little or no sorbitol anhydride esters. In contrast, transesterification with fatty acid methyl esters under basic conditions results in a product in which about half of the sorbitol fatty acid esters are esters of sorbitol anhydrides. Formation of the anhydrides serves to direct esterification to formation of tetraesters, since two of the six hydroxy groups of sorbitol are thereby made unavailable for esterification. Thus, the present invention is also directed to the composition wherein at least a portion of the sorbitol tetraesters are in the anhydride form.

Moreover, the process for preparing the mixture of sorbitol fatty acid esters and sorbitol anhydride fatty acid esters with an average degree of substitution of about 4 fatty acid groups also forms a part of the present invention. In this process, a mixture of sorbitol, an alkali metal fatty acid soap, an excess of a fatty acid alkyl ester and an appropriate catalyst is heated to a temperature, for example, from about 120° C. to about 180° C., and for a time, for example, about 4 hours, sufficient to effect the desired degree of esterification.

Preferred catalysts which may be used in the process of the present invention are basic catalysts such as, for example, alkali metal catalysts. Preferred alkali metal catalysts include potassium metal, sodium metal, potassium hydride, sodium hydride, potassium hydroxide, sodium hydroxide; alkali metal alkoxides such as potassium methoxide, potassium ethoxide, potassium t-butoxide, sodium methoxide, sodium ethoxide; and other alkali metal catalysts such as potassium carbonate and sodium carbonate, the latter two catalysts being especially preferred.

Preferred fatty acid alkyl esters which may be used in the process of the present invention are the fatty acid methyl esters.

Preferably, the process is conducted under solvent-free conditions.

The fat substitute, or fat mimetics, of the present invention may be incorporated into a variety of foodstuffs and are useful as a replacement of at least a portion of the naturally occurring triglycerides. Representative foodstuffs which can contain the sorbitol tetraester in full or partial replacement for naturally occurring fats are: frozen desserts such as ice cream, frozen yogurt or milk shakes; puddings and pie fillings; margarine substitutes or blends; flavored bread or biscuit spreads; mayonnaise; salad dressings; salad oils, filled products such as filled cream or filled milk; cheeses; sour cream; snack food coatings; dairy or non-dairy cheese spreads; liquid or dry coffee lighteners; flavored dips; frying fats and oils; reformed and comminuted meats; meat substitutes and extenders; whipped toppings; compound coatings; soups, gravies, or sauces; frostings and fillings; cocoa butter replacements or blends; fat-containing candies such as those containing peanut butter or chocolate; and bakery products such as cakes, breads, rolls, pastries, cookies, biscuits and crackers. The fat mimetics of the present invention may also be used as a fat substitute in cooking or frying sprays used to coat utensils so as to result in a non-sticky surface.

The sorbitol fatty acid tetraesters of the present invention show advantages over highly esterified polyol polyesters. By virtue of their partial esterification, the sorbitol tetraesters are partially hydrolyzed by mammalian intestinal lipases. While it is not intended that the invention be bound by theory, it is believed that nonmetabolizable fat substitutes hinder absorption of fat-soluble vitamins and other lipophilic nutrients by partitioning them (i.e., extracting them) into the oil phase of the intestinal contents, and that this process is greatly diminished in the partially hydrolysed sorbitol esters. It is further believed that anal leakage is minimized by the partially hydrolyzed esters, whose surfactant properties facilitate emulsification within the gastrointestinal tract.

Sorbitol fatty acid esters with a degree of substitution of about 4 also show a caloric availability of about 15%, which is believed to be a suitable compromise between caloric availability on one hand, and a minimization of side effects on the other.

The invention having been described in general terms, reference is now made to specific examples, it being understood that these examples are not meant to limit the present invention, the scope of which is determined by the appended claims.

EXAMPLE 1

Sorbitol Tetraoleate

A solution of 0.6 gram of potassium hydroxide and 23.75 grams of methyl oleate in about 50 milliliters of methanol was heated to reflux for two hours. With stirring, 1.82 grams of sorbitol and 0.5 gram of sodium carbonate were added and heating was continued, with a nitrogen purge to assist in removal of methanol by distillation. When the temperature of the reaction mixture reached 120° C., pressure in the reaction vessel was reduced to about 10-15 mm Hg for about one hour. The pressure was then further reduced to about 1 mm Hg and the temperature was increased to 155° C. for 3.5 hours. The reaction mixture was then cooled to about 90° C., vigorously stirred with 30 milliliters of water and 10 milliliters of saturated sodium chloride solution, and centrifuged at room temperature for 45 minutes at 8000 rpm. The resulting mixture had three layers: an oil layer on top, an aqueous layer on the bottom, and a thick soap in the middle. The oil layer was decanted from the soap. The water-soap mixture was filtered and washed with a small amount of hexane to dissolve oil entrained in the soap. The hexane layer was separated and added to the oil, and the resulting solution was evaporated to a clear, dark oil. chromatography on a silica gel column with a 30:70 ether-hexane mixture gave a 6.85-gram fraction of impure sorbitol esters. Chromatography of this material under the same conditions gave 1.51 grams of sorbitol esters, which were found by gas chromatographic analysis to have an average degree of substitution of 3.9.

EXAMPLE 2

Soybean Fatty Acid Tetraester of Sorbitol

A solution of 1.8 grams of potassium hydroxide pellets (approximately 87% KOH) and 100 grams of soybean oil fatty acid methyl esters in about 100 milliliters of methanol was heated to reflux for two hours. With stirring, 6.7 grams of sorbitol and 1.5 gram of potassium carbonate were added and heating was continued, with a nitrogen purge to assist in removal of methanol by distillation. The oil bath temperature was increased to 155° C. and the pressure in the reaction vessel was reduced to about 8-10 mm Hg for about two hours, then to about 3 mm Hg for about two hours. The reaction mixture was allowed to cool to about 100° C., stirred with 100 milliliters of water and 50 milliliters of saturated sodium chloride solution, and centrifuged. The resulting mixture had three layers: an oil layer on top, an aqueous layer on the bottom, and a thick soap in the middle. The oil layer was decanted from the soap, washed with methanol, concentrated to approximately 50 grams of a dark yellow oil, and dissolved in hexane. The resulting solution was treated with 2.5 grams of activated carbon on a steam bath for 15 minutes, then filtered through Filtrol 105 (Harshaw-Filtrol-Englehard acid-activated clay absorbent) and evaporated to 27 grams of a clear, pale yellowish oil. About 10 grams of the oil was extracted with methanol for 18 hours to remove excess fatty acid methyl esters. The purified oil was isolated and subjected to vacuum stripping to remove residual methanol, yielding 7.9 grams of sorbitol esters as a clear oil. By gas chromatographic analysis, the average degree of substitution was 3.7 fatty acid groups per sorbitol group. Optionally, the product may be further purified by steam distillation to remove volatile impurities.

EXAMPLE 3

Corn Oil Fatty Acid Tetraester of Sorbitol

A solution of 0.9 gram of potassium hydroxide and 50 grams of corn oil fatty acid methyl esters in about 70 milliliters of methanol was heated to reflux for two hours. With stirring, 3.64 grams of sorbitol and 0.82 gram of potassium carbonate were added and heating was continued, with a nitrogen purge to assist in removal of methanol by distillation. When the temperature of the reaction mixture reached 155°–160° C., pressure in the reaction vessel was reduced to about 10-15 mm Hg for two hours, then to about 2 mm Hg for two hours. The reaction mixture was cooled to about 110° C., then vigorously stirred with 75 milliliters of water and 50 milliliters of saturated sodium chloride solution. The two-phase mixture was centrifuged at room temperature for 45 minutes at 9000 rpm. The oil layer was decanted from the soap and aqueous layers and diluted to 250–300 milliliters with hexane. The hexane solution was washed with an equal volume of methanol, treated with activated carbon and Filtrol 105 on a steam bath, filtered through Filtrol 105, and evaporated to 29.7 grams of a yellow oil. The oil was extracted with methanol for 18 hours to remove excess fatty acid methyl esters, then vacuum stripped to 17.9 grams of yellow oil.

EXAMPLE 4

Sunflower Oil Fatty Acid Tetraester of Sorbitol

The procedure of Example 3 was repeated, substituting 50 grams of sunflower oil fatty acid methyl esters for the corn oil esters used in Example 3. The product after methanol extraction was 13.1 grams of a clear yellow oil.

EXAMPLE 5

Safflower Oil Fatty Acid tetraester of Sorbitol

The procedure of Example 3 was repeated, substituting 50 grams of safflower oil fatty acid methyl esters for the corn oil esters used in Example 3. The product after methanol extraction was 15.7 grams of a clear yellow oil.

EXAMPLE 6

Olive Oil Fatty Acid Tetraester of Sorbitol

The procedure of Example 3 was repeated, substituting 50 grams of olive oil fatty acid methyl esters for the corn oil esters used in Example 3. The product after methanol extraction was 15.0 grams of a clear yellow oil.

EXAMPLE 7

French Fried Potatoes

French fried potatoes were cooked in sorbitol soybean fatty acid tetraester under conditions designed to model those encountered in commercial french-frying operations, whereby the same oil is used to cook a number of batches over an extended period of time. Thus, a batch of oil was held at the cooking temperature (approximately 175° C.) for ten-hour periods on four consecutive days, and during each day, ten batches of potatoes were cooked at one-hour intervals. Frozen potatoes which had been par fried in partially hydrogenated soybean oil (Ore Ida Golden Crinkle French Fried Potatoes) were used in the tests. Fresh oil was added to the fryers as required to maintain the initial oil level, and the oil was filtered to remove food particles at the end of each day. Small samples of the oil were removed on each day after the first, fifth, and tenth batches, and analyzed with a commercial test kit (Libra Veri-Fry Diagnostic Quick Test Kit) for total polar materials, free fatty acids, and total alkaline materials. The oil showed a tendency to foam during frying, which was believed to be the result of impurities. In agreement with this hypothesis, it was found to contain higher levels of soaps and free fatty acids than a corresponding commercial cooking oil (Wesson All-Natural soybean oil) held under the same conditions. The fried potatoes were also somewhat greasier to the touch than potatoes fried in the commercial oil, which was consistent with the presence of soaps. However, odor and taste of the fried potatoes remained acceptable throughout the test.

EXAMPLE 8

Lipase Hydrolysis of Sorbitol Esters

Extent of hydrolysis of sorbitol esters by a mixture of porcine enzymes was evaluated by the test procedure described below.

An enzyme solution was prepared by blending 1.5 grams of lipase Type II crude porcine steapsin (Sigma Chemical Company catalog number L 3136), 1.0 gram of porcine pancreatin (Sigma P 1500), and 0.5 gram of porcine pancreatin (Sigma P 7545) with 10 milliliters of water for 30 minutes in a blender, then filtering to obtain a clear solution.

To an accurately weighed 0.5–1 gram sample of the sorbitol ester were added 5.0 milliliters of ethanol, 20 milliliters of pH 9.0 aqueous solution containing 10% gum acacia and 2.5% sodium chloride, 20 milliliters of an aqueous solution containing 1% histidine monohydrochloride and 5.8% sodium chloride, and 0.5 milliliter of 45% calcium chloride solution. With vigorous stirring, the mixture was adjusted to pH 9.0 with 0.05N potassium hydroxide solution. Mixing was continued for 10 minutes to thoroughly emulsify the oil, and 0.5 milliliter of the above enzyme solution was added. With continued stirring, 0.05M potassium hydroxide solution was added at a rate sufficient to maintain pH 9.0. The rate of addition of the potassium hydroxide solution was monitored for 10 minutes. Rate of hydrolysis was calculated by the following equation:

$$\text{Lipase units per gram} = \frac{\text{Rate of KOH addition (ml/min)} \times 50}{\text{Weight of sample (grams)}}$$

Percent lipase hydrolysis data for sorbitol esters, calculated as ratios of rate of hydrolysis of the esters divided by rate of hydrolysis of a soybean oil standard, are given in Table 1.

TABLE 1

Lipase Hydrolysis Data

| Oil | Percent Lipase Hydrolysis |
|---|---|
| Soybean oil (standard) | (100) |
| Sorbitol tetraoleate | 24.0 |
| Soybean fatty acid tetraester of sorbitol | 20.0 |

EXAMPLE 9

Radiolabeled Sorbitol Tetraoleate

A solution of 20 grams of oleic acid, 1.0 millicurie of $^{14}$C-labeled oleic acid, and 20 milliliters of boron trifluoride etherate in ethanol was heated to reflux overnight. The solution was cooled, diluted with water, and extracted with ether. The ether extract was washed with water and saturated sodium chloride solution, dried with anhydrous magnesium sulfate, and evaporated to 24.5 milliliters of radiolabeled ethyl oleate as a colorless liquid. A solution of 20 grams of this material and 0.36 gram of potassium hydroxide in 25 milliliters of methanol was heated to reflux for two hours. With stirring, 1.34 grams of sorbitol, 0.5 millicurie of $^{14}$C-labeled sorbitol, and 0.3 gram of potassium carbonate were added and heating was continued, with a nitrogen purge to assist in removal of methanol by distillation. When the temperature of the reaction mixture reached 155°–160° C., pressure in the reaction vessel was reduced to about 10–15 mm Hg for five hours. The reaction mixture was cooled to about 100° C., then vigorously stirred with about 20 milliliters of water and 20 milliliters of saturated sodium chloride solution. The two-phase mixture was centrifuged at room temperature for about 45 minutes at 8000–9000 rpm. The oil layer was decanted from the soap and aqueous layers and dissolved in hexane. The hexane solution was filtered through Filtrol 105 and evaporated to an oil, which was extracted with methanol for 18 hours to remove excess fatty acid methyl esters, then vacuum stripped to 5.01 grams of a clear off-white oil. Although the radioactivity of the material did not allow a determination of its degree of substitution by gas chromatography, it was found to be identical by thermogravimetric analysis and thin-layer chromatography to unlabeled sorbitol tetraoleate with an average degree of substitution of 3.9.

EXAMPLE 10

Caloric Utilization of Sorbitol Tetraoleate in Rats

Two groups of four albino rats each were administered, by oral gavage, a single 50 milligram dose of either radiolabeled sorbitol tetraoleate or radiolabeled triolein. The rats were put into metabolism cages, and radioactivity was monitored for 72 hours in expired carbon dioxide, feces, urine, and cage washes by liquid scintillation counting of samples. All animals exhibited normal fecal pellets throughout the monitoring period, suggesting that the test material did not cause anal leakage. The animals were sacrificed, and radioactivity was determined in liver and adipose tissue. Due to adherence of the oily samples to the plastic syringes used for dosing, total recovery of radioactivity could not be calculated. However, the distribution of recovered $^{14}C$, being independent of the total amount administered, indicated very different metabolic pathways for sorbitol tetraoleate and triolein. These data, given in Table 2, demonstrate that 85% of administered sorbitol tetraoleate is excreted directly, leaving 15% available for caloric utilization.

TABLE 2

Distribution of $^{14}C$ Recovered from Rats

| Test Substance | $CO_2$ | Urine | Feces | Cage | Liver | Fat | Total |
|---|---|---|---|---|---|---|---|
| Sorbitol tetraoleate | 4.8 | 3.6 | 85.0 | 4.8 | 0.2 | 1.4 | 99.8 |
| Triolein | 85.1 | 2.2 | 2.1 | 0.0 | 1.0 | 9.6 | 100.0 |

We claim:

1. An edible composition consisting essentially of a liquid sorbitol fatty acid ester with a degree of substitution of about 4 fatty acid groups derived from a mixture of fatty acids provided that not all of the fatty acid groups of said ester are derived from oleic acid, at least a portion of said ester in the anhydride form, said composition useful as a low calorie fat substitute having a caloric availability of from about 10% to about 33%, said sorbitol ester resulting in less depletion of fat soluble nutrients when fed in a liquid form to a mammal than a fully esterified polyol fatty acid polyester, said composition having a functionality similar to that of cooking oil.

2. A composition according to claim 1 wherein said degree of substitution ranges from about 3.6 to about 4.4.

3. A composition according to claim 1 wherein said degree of substitution is about 3.8.

4. A composition according to claim 1 wherein the fatty acid groups of said fatty acid ester are selected from the group consisting of synthetic, natural, saturated, unsaturated, straight chain and branched chain fatty acids; and mixtures thereof.

5. A composition according to claim 1 wherein the fatty acid groups of said fatty acid ester are selected from the group consisting of butyric, caproic, caprylic, pelargonic, capric, undecanoic, lauric, myristic, palmitic, oleic, elaidic, myristoleic, palmitoleic, ricinoleic, erucic, stearic, arachidic, behenic, linoleic, linolenic, eleostearic, and arachidonic acids; fatty acid derivatives; and mixtures thereof.

6. A composition according to claim 1 wherein the fatty acid groups of said fatty acid ester are obtained from oils selected from the group consisting of non-hydrogenated, partially hydrogenated, or hydrogenated oils selected from the group consisting of soybean oil, safflower oil, sunflower oil, sesame oil, peanut oil, corn oil, olive oil, rice bran oil, canola oil, rapeseed oil, shea nut oil, babassu nut oil, coconut oil, palm kernel oil, cottonseed oil, and palm oil; butterfat; tallow, and lard; and mixtures thereof.

7. A composition according to claim 6 wherein the fatty acid group of said fatty acid ester is obtained from non-hydrogenated, partially hydrogenated, or hydrogenated soybean oil.

8. A triglyceride-containing foodstuff having at least a portion of the normally present triglyceride replaced by a composition comprising a sorbitol fatty acid ester with a degree of substitution of about 4 fatty acid groups at least a portion of said ester in the anhydride form, said sorbitol fatty acid ester having a caloric availability of from about 10% to about 33%, said sorbitol ester resulting in less depletion of fat soluble nutrients when fed in a liquid form to a mammal than a fully esterified polyol fatty acid polyester, said composition having a functionality similar to that of cooking oil.

9. A foodstuff according to claim 8 wherein said foodstuff is a frozen dessert.

10. A foodstuff according to claim 8 wherein said foodstuff is selected from the group consisting of salad dressings and salad oils.

11. A foodstuff according to claim 8 wherein said foodstuff is selected from the group consisting of dips for crackers, dips for chips, and dips for vegetables.

12. A foodstuff according to claim 8 wherein said foodstuff is a spread.

13. A foodstuff according to claim 8 wherein said foodstuff is a whipped topping.

14. A foodstuff according to claim 8 wherein said foodstuff is a triglyceride-containing confection.

15. A foodstuff according to claim 8 wherein said foodstuff is selected from the group consisting of frostings or icings for cakes and frostings or icings for cookies.

16. A foodstuff according to claim 8 wherein said foodstuff is selected from the group consisting of fillings for cakes and fillings for cookies.

17. A foodstuff according to claim 8 wherein said foodstuff is selected from the group consisting of whipped desserts, and gelled desserts.

18. A foodstuff according to claim 8 wherein said foodstuff is a beverage.

19. A foodstuff according to claim 8 wherein said foodstuff is a shortening or frying oil.

20. A foodstuff according to claim 8 wherein said foodstuff is selected from the group consisting of soups, gravies and sauces.

21. A foodstuff according to claim 8 wherein said foodstuff is baked goods.

22. A foodstuff according to claim 8 wherein said foodstuff is selected from the group consisting of mayonnaise and imitation mayonnaise.

23. A foodstuff according to claim 8 wherein said foodstuff is a liquid or dry imitation dairy product.

24. A foodstuff according to claim 8 wherein said foodstuff is a liquid or plastic margarine spread.

25. A foodstuff according to claim 8 wherein said foodstuff is a pasta.

26. A foodstuff according to claim 8 wherein said foodstuff is selected from the group consisting of meat analogues, poultry analogues and fish analogues.

27. A foodstuff according to claim 8 wherein said foodstuff is a cooking or frying spray.

28. A foodstuff according to claim 8 wherein said foodstuff is a coating for snack foods.

29. A method of reducing the fat content of a foodstuff containing triglycerides comprising replacing at least a portion of the normally present triglyceride by a composition comprising a sorbitol fatty acid ester with a degree of substitution of about 4 fatty acid groups at least a portion of said ester in the anhydride form, said sorbitol fatty acid ester having a caloric availability of from about 10% to about 33%, said sorbitol ester resulting in less depletion of fat soluble nutrients when fed in a liquid form to a mammal than a fully esterified polyol fatty acid polyester, said composition having a functionality similar to that of cooking oil.

30. A method according to claim 29 wherein said foodstuff is a frozen dessert.

31. A method according to claim 29 wherein said foodstuff is selected from the group consisting of salad dressings and salad oils.

32. A method according to claim 29 wherein said foodstuff is selected from the group consisting of dips for crackers, dips for chips, and dips for vegetables.

33. A method according to claim 29 wherein said foodstuff is a spread.

34. A method according to claim 29 wherein said foodstuff is a whipped topping.

35. A method according to claim 29 wherein said foodstuff is a triglyceride containing confection.

36. A method according to claim 29 wherein said foodstuff is selected from the group consisting of frostings or icings for cakes and frostings or icings for cookies.

37. A method according to claim 29 wherein said foodstuff is selected from the group consisting of fillings for cakes and fillings for cookies.

38. A method according to claim 29 wherein said foodstuff is selected from the group consisting of whipped desserts and gelled desserts.

39. A method according to claim 29 wherein said foodstuff is a beverage.

40. A method according to claim 29 wherein said foodstuff is a shortening or frying oil.

41. A method according to claim 29 wherein said foodstuff is selected from the group consisting of soups, gravies and sauces.

42. A method according to claim 29 wherein said foodstuff is baked goods.

43. A method according to claim 29 wherein said foodstuff is selected from the group consisting of mayonnaise and imitation mayonnaise.

44. A method according to claim 29 wherein said foodstuff is a liquid or dry imitation dairy product.

45. A method according to claim 29 wherein said foodstuff is a liquid or plastic margarine spread.

46. A method according to claim 29 wherein said foodstuff is a pasta.

47. A method according to claim 29 wherein said foodstuff is selected from the group consisting of meat analogues, poultry analogues and fish analogues.

48. A method according to claim 29 wherein said foodstuff is a cooking or frying spray.

49. A method according to claim 29 wherein said foodstuff is a coating for snack foods.

\* \* \* \* \*